(12) United States Patent
Liang

(10) Patent No.: US 11,091,416 B2
(45) Date of Patent: Aug. 17, 2021

(54) CATALYST FOR PREPARING PROPYLENE GLYCOL PHENYL ETHER AND METHOD FOR SYNTHESIZING PROPYLENE GLYCOL PHENYL ETHER

(71) Applicant: Jiahua Chemicals (Maoming) Co., Ltd., Guangdong (CN)

(72) Inventor: Guoqiang Liang, Guangdong (CN)

(73) Assignee: Jiahua Chemicals (Maoming) Co., Ltd., Guangong (CN)

( * ) Notice: Subject to any disclaimer, the term of this patent is extended or adjusted under 35 U.S.C. 154(b) by 0 days.

(21) Appl. No.: 16/627,938

(22) PCT Filed: Aug. 17, 2018

(86) PCT No.: PCT/CN2018/101121
§ 371 (c)(1),
(2) Date: Dec. 31, 2019

(87) PCT Pub. No.: WO2019/034149
PCT Pub. Date: Feb. 21, 2019

(65) Prior Publication Data
US 2020/0157030 A1 May 21, 2020

(30) Foreign Application Priority Data
Aug. 18, 2017 (CN) .......................... 201710712994.3

(51) Int. Cl.
*C07C 41/03* (2006.01)
*C07C 43/23* (2006.01)
(52) U.S. Cl.
CPC .............. *C07C 41/03* (2013.01); *C07C 43/23* (2013.01); *C07C 2527/14* (2013.01); *C07C 2531/24* (2013.01)
(58) Field of Classification Search
CPC ...... C07C 41/03; C07C 43/23; C07C 2527/14
See application file for complete search history.

(56) References Cited

U.S. PATENT DOCUMENTS 4,011,268 A   3/1977   McKinley et al.

FOREIGN PATENT DOCUMENTS

| CN | 101333285 A | 12/2008 |
| CN | 101712600 A | 5/2010 |
| CN | 102240539 A | 11/2011 |
| CN | 105921172 A | 9/2016 |
| CN | 106187712 A | 12/2016 |
| CN | 106478385 A | 3/2017 |
| CN | 107684602 A | 2/2018 |
| CN | 107694602 A | 2/2018 |
| DE | 2157455 A1 | 5/1973 |
| JP | S5065 B1 | 1/1975 |
| JP | S50654 B1 | 1/1975 |

OTHER PUBLICATIONS

First Office Action issued in priority CN application 201710712994.3 dated Apr. 19, 2019.
International Search Report and Written Opinion, received in international patent application No. PCT/CN2018/101121, dated Nov. 1, 2018, 17 pages, including English translations.
Extended European Search Report dated May 7, 2020, received in international patent application No. PCT/CN2018/101121, 7 pages.

*Primary Examiner* — Sikarl A Witherspoon
(74) *Attorney, Agent, or Firm* — Verrill Dana, LLP

(57) ABSTRACT

Disclosed is a method for preparing propylene glycol phenyl ether, comprising carrying out a polymerization reaction of phenol and a propylene oxide in the presence of a quaternary phosphonium salt compound as a catalyst. Preferably, the method comprises mixing phenol and a quaternary phosphonium salt compound, and then adding propylene oxide under oxygen-free conditions, wherein the phenol is polymerized with the propylene oxide to produce the propylene glycol phenyl ether. The propylene glycol phenyl ether thus prepared has few impurities and contains no metal ions, such as potassium and sodium, and does not require subsequent operations to remove metal ions and perform rectification separation, thereby reducing the costs and allowing same to be directly applied to high-standard industrial production.

7 Claims, No Drawings

CATALYST FOR PREPARING PROPYLENE GLYCOL PHENYL ETHER AND METHOD FOR SYNTHESIZING PROPYLENE GLYCOL PHENYL ETHER

CROSS-REFERENCE TO RELATED APPLICATIONS

This application is a National Stage Entry of International Patent Application No. PCT/CN2018/101121 with an international filing date of Aug. 17, 2018, designating the United States, now pending, and further claims priority benefits to Chinese Patent Application No. 201710712994.3, filed on Aug. 18, 2017. The contents of all of the aforementioned applications are incorporated herein by reference.

TECHNICAL FIELD

The present invention belongs to the technical field of chemical industry, and particularly relates to a catalyst for preparing propylene glycol phenyl ether and a method for synthesizing propylene glycol phenyl ether.

BACKGROUND

Propylene glycol phenyl ether is a colorless transparent liquid with mild odor, and is non-toxic and environmentally friendly. Propylene glycol phenyl ether is a typical high-efficiency film-forming auxiliary. After adding into a latex system, propylene glycol phenyl ether can be redistributed in the aqueous phase and the polymerization phase, with an extremely small distribution coefficient in both phases, thereby ensuring excellent film-forming performance, good plasticizing-effect and the appropriate evaporation rate balance. Propylene glycol phenyl ether has a strong solubility in most latexes and has a poor water-solubility, ensuring complete absorption by the latex particles and thereby allowing the latex paint to have the best color uniformity, coalescence performance, and excellent storage stability. Propylene glycol phenyl ether can also be used as an excellent high-boiling organic solvent and an modification auxiliary to replace solvents that have higher toxicity and heavier odor, such as isophorone, cyclohexanone, benzyl alcohol or ethylene glycol phenyl ether. Propylene glycol phenyl ether is widely used in areas such as automobile and automobile paint repair, electrophoretic paint, industrial baking enamel and ship, container and wood coating, due to its non-toxicity, good miscibility, moderate volatilization rate, excellent coalescence and coupling ability, and low surface tension.

At present, propylene glycol phenyl ether is generally produced with two synthetic processes. One process is to produce propylene glycol phenyl ether by using chloropropanol and phenol as reaction substrates, but a large amount of waste is easily produced when chloropropanol is used as a substrate. The second process for synthesizing propylene glycol phenyl ether is to carry out ring-opening polymerization of phenol and propylene oxide (PO) in the presence of a basic catalyst such as sodium hydroxide or potassium hydroxide. The second process is an industrial production method mainly used at present, but the propylene glycol phenyl ether product synthesized by using the above catalyst contains metal ions such as potassium and sodium ions, and thus cannot be directly applied to industrial fields where metal ions are strictly restricted. Subsequent processing is required to remove metal ions, resulted in complexity in the operation of the entire process as well as increased production cost of propylene glycol phenyl ether.

SUMMARY OF THE INVENTION

The present invention is designed to overcome the defects that the propylene glycol phenyl ether synthesized by using the catalyst in the prior art contains metal ions and thus cannot be directly applied to industrial fields where metal ions are strictly restricted, and that subsequent processing is required to remove metal ions, resulted in complexity in the operation of the entire process as well as increased production cost of propylene glycol phenyl ether. For this purpose, the present invention provides a catalyst suitable for use in preparing propylene glycol phenyl ether which is free of metal ions and does not need subsequent processing to remove metal ions.

In a first aspect, the present invention provides a method for preparing propylene glycol phenyl ether, comprising carrying out a polymerization reaction of phenol and a propylene oxide in the presence of a quaternary phosphonium salt compound as a catalyst.

In the above method for preparing propylene glycol phenyl ether, preferably, the quaternary phosphonium salt compound is selected from the group consisting of methyltriphenylphosphonium bromide, ethyltriphenylphosphonium bromide, propyltriphenylphosphonium bromide, butyltriphenylphosphonium bromide, and any combination thereof.

In the above method for preparing propylene glycol phenyl ether, preferably, each constituent in the combination is present in an amount of 1 to 99 parts by molar.

In the method for preparing propylene glycol phenyl ether, wherein said carrying out a polymerization reaction comprises the steps of: preparing a mixture by mixing phenol with the above quaternary phosphonium salt compound, and carrying out the polymerization reaction of the phenol and the propylene oxide by adding the propylene oxide into the mixture under oxygen-free conditions, producing a propylene glycol phenyl ether.

In the above method for preparing propylene glycol phenyl ether, preferably, a molar ratio of the phenol to the propylene oxide is 1:(1-1.15).

In the above method for preparing propylene glycol phenyl ether, preferably, the quaternary phosphonium salt compound is added in an amount of from 0.05% to 0.3% by mass based on a total mass of the phenol and the propylene oxide.

In the above method for preparing propylene glycol phenyl ether, preferably, the polymerization reaction is carried out at a temperature of 100° C. to 160° C. and a pressure of less than or equal to 1.0 MPa.

Preferably, the above method for preparing propylene glycol phenyl ether further comprises a step of raising the temperature to 80° C. and controlling the temperature to be 80° C. to 160° C. and the pressure to be less than or equal to 1.0 MPa prior to adding the propylene oxide, and then adding the propylene oxide Preferably, the above method for preparing propylene glycol phenyl ether further comprises the steps of: controlling the temperature at 100° C. to 160° C. and aging for 2 h to 10 h after adding the propylene oxide to obtain the propylene glycol phenyl ether; and then controlling the temperature at 100° C. to 130° C. and performing vacuum pumping at the temperature of 100° C. to 130° C.

The present invention has the following advantages over the prior art:

1. In the use of a quaternary phosphonium salt compound as a catalyst for preparing propylene glycol phenyl ether provided by the present invention, the quaternary phosphonium salt compound has high catalytic efficiency as a catalyst, and the produced propylene glycol phenyl ether is free of metal ions such as potassium and sodium ions, thereby improving the quality and environmental friendliness of the products. By using the quaternary phosphonium salt as a catalyst to prepare propylene glycol phenyl ether, no subsequent process for removing metal ions is required, so the production process is simplified and the production cost is reduced. The quaternary phosphonium salt compound has high relative stability as a catalyst, and thus the produced propylene glycol phenyl ether has stable quality and good repeatability between batches, and the requirements for the reaction conditions and the strength of the equipment are reduced.

2. The quaternary phosphonium salt compound provided by the present invention as a catalyst for preparing propylene glycol phenyl ether is selected from the group consisting of methyltriphenylphosphonium bromide, ethyltriphenylphosphonium bromide, propyltriphenylphosphonium bromide, butyltriphenylphosphonium bromide, and any combination thereof. As a catalyst for preparing propylene glycol phenyl ether, the above-mentioned compounds have high thermal stability, easy availability and no pollution, and do not need to be separated from the product, so the production cost of propylene glycol phenyl ether is reduced and the influence of the synthesis process on the environment is reduced. Therefore, it is an economic and environmentally friendly catalyst.

3. In the method for synthesizing propylene glycol phenyl ether provided by the present invention, by using the above quaternary phosphonium salt compound as a catalyst, the produced propylene glycol phenyl ether is free of metal ions, so no subsequent removal of metal ions is required, and thus the quality of the product is improved, operation of the entire synthesis process is simplified, and the production cost of propylene glycol phenyl ether is reduced.

4. In the method for synthesizing propylene glycol phenyl ether provided by the present invention, by controlling the reaction temperature, pressure, time, and the ratio of phenol to propylene oxide, the dosage of the catalysts is reduced without affecting the catalytic activity and product quality. The produced propylene glycol phenyl ether has few impurities and does not require subsequent rectification purification, and can be directly applied to industrial production and application.

5. The method for preparing propylene glycol phenyl ether provided by the present invention ensures high catalytic activity of the catalyst by controlling the temperature and pressure of the reaction, and unreacted substrates are effectively removed by the vacuum pumping performed after the reaction is completed.

DETAILED DESCRIPTION OF EMBODIMENTS

The implementation of the present invention will be illustrated by the following specific embodiments. Unless otherwise stated, the experimental methods disclosed in the present invention are all based on the conventional technical means in the art, and the reagents and raw materials used in the embodiments are commercially available.

Embodiment 1

Provided is a method for synthesizing propylene glycol phenyl ether, specifically comprising the following steps:

(1) Adding 10 mol phenol to a 2 liter high-pressure reactor; and adding 10 mol propylene oxide to a metering tank.

(2) Then adding methyltriphenylphosphonium bromide to the reactor as a catalyst in an amount of 0.05% by mass based on a total mass of the phenol and the propylene oxide. Performing nitrogen replacement after the reactor was closed. Then raising the temperature to 80° C., and adding the propylene oxide from the metering tank to the reactor, and continue raising the temperature, and controlling the temperature to be 100° C. to 110° C. and the pressure to be less than or equal to 1.0 MPa.

(3) After the adding of propylene oxide is completed, closing the propylene oxide feed valve and keeping the temperature at 100° C. to 110° C. for 8 h to carry out a polymerization reaction. Controlling the temperature at 100° C. to 110° C. after the reaction is completed, and performing vacuum pumping for 1 h and then cooling the temperature to below 80° C., producing a propylene glycol phenyl ether product.

Embodiment 2

Provided is a method for synthesizing propylene glycol phenyl ether, specifically comprising the following steps:

(1) Adding 10 mol phenol to a 2 liter high-pressure reactor; and adding 10.3 mol propylene oxide to a metering tank.

(2) Then adding ethyltriphenylphosphonium bromide to the reactor as a catalyst in an amount of 0.2% by mass based on a total mass of the phenol and the propylene oxide. Performing nitrogen replacement after the reactor was closed. Then raising the temperature to 80° C., and adding propylene oxide from the metering tank to the reactor, and continue raising the temperature, and controlling the temperature to be 100° C. to 110° C. and the pressure to be less than or equal to 1.0 MPa.

(3) After the adding of propylene oxide is completed, closing the propylene oxide feed valve and keeping the temperature at 130° C. to 140° C. for 4 h to carry out a polymerization reaction. Controlling the temperature at 110° C. to 120° C. after the reaction is completed, and performing vacuum pumping for 2.5 h and then cooling the temperature to below 80° C., producing a propylene glycol phenyl ether product.

Embodiment 3

Provided is a method for synthesizing propylene glycol phenyl ether, specifically comprising the following steps:

(1) Adding 10 mol phenol to a 2 liter high-pressure reactor; and adding 10.5 mol propylene oxide to a metering tank.

(2) Then adding propyltriphenylphosphonium bromide to the reactor as a catalyst in an amount of 0.3% by mass based on a total mass of the phenol and the propylene oxide. Performing nitrogen replacement after the reactor was closed. Then raising the temperature to 80° C., and adding the propylene oxide from the metering tank to the reactor, and continue raising the temperature, and controlling the temperature to be 150° C. to 160° C. and the pressure to be less than or equal to 1.0 MPa.

(3) After the adding of propylene oxide is completed, closing the propylene oxide feed valve and keeping the temperature at 150° C. to 160° C. for 4 h to carry out a polymerization reaction. Controlling the temperature at 120° C. to 130° C. after the reaction is completed, and performing vacuum pumping for 2 h and then cooling the temperature to below 80° C., producing a propylene glycol phenyl ether product.

Embodiment 4

Provide is a method for synthesizing propylene glycol phenyl ether, specifically comprising the following steps:

(1) Adding 10 mol phenol to a 2 liter high-pressure reactor; and adding 11 mol propylene oxide to a metering tank.

(2) Then adding butyltriphenylphosphonium bromide to the reactor as a catalyst in an amount of 0.3% by mass based on a total mass of the phenol and the propylene oxide. Performing nitrogen replacement after the reactor was closed. Then raising the temperature to 80° C., and adding the propylene oxide from the metering tank to the reactor, and continue raising the temperature, and controlling the temperature to be 120° C. to 130° C. and the pressure to be less than or equal to 1.0 MPa.

(3) After the adding of propylene oxide is completed, closing the propylene oxide feed valve and keeping the temperature at 130° C. to 140° C. for 2 h to carry out a polymerization reaction. Controlling the temperature at 110° C. to 120° C. after the reaction is completed, and performing vacuum pumping for 3 h and then cooling the temperature to below 40° C., producing a propylene glycol phenyl ether product.

Embodiment 5

Provided is a method for synthesizing propylene glycol phenyl ether, specifically comprising the following steps:

(1) Adding 10 mol phenol to a 2 liter high-pressure reactor; and adding 11.5 mol propylene oxide to a metering tank.

(2) Then adding a mixture of methyltriphenylphosphonium bromide and ethyltriphenylphosphonium bromide to the reactor as a catalyst in an amount of 0.15% by mass based on a total mass of the phenol and the propylene oxide, wherein the methyltriphenylphosphonium bromide is present in an amount of 1 part by molar, and the ethyltriphenylphosphonium bromide is present in an amount of 99 parts by molar. Performing nitrogen replacement after the reactor was closed. Then raising the temperature to 80° C., and adding the propylene oxide from the metering tank to the reactor, and continue raising the temperature, and controlling the temperature to be 100° C. to 110° C. and the pressure to be less than or equal to 1.0 MPa.

(3) After the adding of propylene oxide is completed, closing the propylene oxide feed valve and keeping the temperature at 120° C. to 130° C. for 4 h to carry out a polymerization reaction. Controlling the temperature at 100° C. to 110° C. after the reaction is completed, and performing vacuum pumping for 3 h and then cooling the temperature to below 80° C., producing a propylene glycol phenyl ether product.

Embodiment 6

Provided is a method for synthesizing propylene glycol phenyl ether, specifically comprising the following steps:

(1) Adding 10 mol phenol to a 2 liter high-pressure reactor; and adding 11.3 mol propylene oxide to a metering tank.

(2) Then adding a mixture of ethyltriphenylphosphonium bromide and propyltriphenylphosphonium bromide to the reactor as a catalyst in an amount of 0.1% by mass based on a total mass of the phenol and the propylene oxide, wherein the ethyltriphenylphosphonium bromide is present in an amount of 30 parts by molar and the propyltriphenylphosphonium bromide is present in an amount of 70 parts by molar. Performing nitrogen replacement after the reactor was closed. Then raising the temperature to 80° C., and adding the propylene oxide from the metering tank to the reactor, and continue raising the temperature, and controlling the temperature to be 150° C. to 160° C. and the pressure to be less than or equal to 1.0 MPa.

(3) After the adding of propylene oxide is completed, closing the propylene oxide feed valve and keeping the temperature at 100° C. to 120° C. for 6 h to carry out a polymerization reaction. Controlling the temperature at 105° C. to 115° C. after the reaction is completed, and performing vacuum pumping for 3 h and then cooling the temperature to below 80° C., producing a propylene glycol phenyl ether product.

Embodiment 7

Provided is a method for synthesizing propylene glycol phenyl ether, specifically comprising the following steps:

(1) Adding 10 mol phenol to a 2 liter high-pressure reactor; and adding 10.1 mol propylene oxide to a metering tank.

(2) Then adding a mixture of methyltriphenylphosphonium bromide, ethyltriphenylphosphonium bromide, propyltriphenylphosphonium bromide and butyltriphenylphosphonium bromide to the reactor as a catalyst in an amount of 0.3% by mass based on a total mass of the phenol and the propylene oxide, wherein the methyltriphenylphosphonium bromide is present in an amount of 1 part by molar, the ethyltriphenylphosphonium bromide is present in an amount of 25 parts by molar, the propyltriphenylphosphonium bromide is present in an amount of 25 parts by molar, and the butyltriphenylphosphonium bromide is present in an amount of 49 parts by molar. Performing nitrogen replacement after the reactor was closed. Then raising the temperature to 80° C., and adding the propylene oxide from the metering tank to the reactor, and continue raising the temperature, and controlling the temperature to be 150° C. to 160° C. and the pressure to be less than or equal to 1.0 MPa.

(3) After the adding of propylene oxide is completed, closing the propylene oxide feed valve and keeping the temperature at 150° C. to 160° C. for 4 h to carry out a polymerization reaction. Controlling the temperature at 120° C. to 130° C. after the reaction is completed, and performing vacuum pumping for 2 h and then cooling the temperature to below 80° C., producing a propylene glycol phenyl ether product.

Test Example 1

The propylene glycol phenyl ether products prepared in Embodiments 1-7 were analyzed with a flame photometer to detect the content of metal ions, and were analyzed with an AquaTint automatic colorimeter (purchased from Lovibond, Germany) to detect the chromaticity. The results are shown in Table 1:

TABLE 1

Test results of propylene glycol phenyl ether products prepared by the method described in Embodiments 1-7.

| | Chromaticity (APHA) | Potassium ion (ppm) | Sodium ion (ppm) |
|---|---|---|---|
| Embodiment 1 | 10 | 0 | 0 |
| Embodiment 2 | 5 | 0 | 0 |
| Embodiment 3 | 10 | 0 | 0 |
| Embodiment 4 | 10 | 0 | 0 |
| Embodiment 5 | 5 | 0 | 0 |
| Embodiment 6 | 15 | 0 | 0 |
| Embodiment 7 | 10 | 0 | 0 |

As can be seen from Table 1, the propylene glycol phenyl ether products prepared by using a quaternary phosphonium salt as a catalyst contains no potassium and sodium ions, and does not require subsequent operations or rectification separation to remove metal ions, so the produced propylene glycol phenyl ether products can be directly applied to industrial areas where metal ion concentration is severely restricted. Meanwhile, the method for synthesizing propylene glycol phenyl ether provided above simplifies the operation process of the whole synthesis process, reduces the synthesis cost of the propylene glycol phenyl ether, and the synthesized propylene glycol phenyl ether products have wide industrial application range.

Apparently, the aforementioned embodiments are merely examples illustrated for clearly describing the present invention, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:

1. A method for preparing propylene glycol phenyl ether, comprising the steps of:
    preparing a mixture by mixing phenol with a quaternary phosphonium salt compound which is selected from the group consisting of methyltriphenylphosphonium bromide, ethyltriphenylphosphonium bromide, propyltriphenylphosphonium bromide, and any combination thereof; and
    carrying out a polymerization reaction of the phenol and a propylene oxide by adding the propylene oxide into the mixture under oxygen-free conditions, the quaternary phosphonium salt compound being added in an amount of from 0.05% to 0.3% by mass based on a total mass of the phenol and the propylene oxide, producing a propylene glycol phenyl ether.

2. The method according to claim 1, wherein each compound in the combination is present in an amount of 1 to 99 parts by molar.

3. The method according to claim 1, wherein a molar ratio of the phenol to the propylene oxide is 1:(1-1.15).

4. The method according to claim 1, wherein the polymerization reaction is carried out at a temperature of 100° C. to 160° C. and a pressure of less than or equal to 1.0 MPa.

5. The method according to claim 4, further comprising a step of raising the temperature to 80° C. and controlling the temperature to be 80° C. to 160° C. and the pressure to be less than or equal to 1.0 MPa prior to adding the propylene oxide, and then adding the propylene oxide.

6. The method according to claim 5, further comprising the steps of: controlling the temperature at 100° C. to 160° C. and aging for 2 h to 10 h after adding the propylene oxide to obtain the propylene glycol phenyl ether; and then controlling the temperature at 100° C. to 130° C. and performing vacuum pumping at the temperature of 100° C. to 130° C.

7. The method according to claim 3, wherein the polymerization reaction is carried out at a temperature of 100° C. to 160° C. and a pressure of less than or equal to 1.0 MPa.

\* \* \* \* \*